United States Patent
Lau et al.

(10) Patent No.: US 7,513,907 B2
(45) Date of Patent: Apr. 7, 2009

(54) EXPANDABLE STENTS AND METHOD FOR MAKING SAME

(75) Inventors: Lilip Lau, Sunnyvale, CA (US); William M. Hartigan, Fremont, CA (US); John J. Frantzen, Copperopolis, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 701 days.

(21) Appl. No.: 11/112,143

(22) Filed: Apr. 22, 2005

(65) Prior Publication Data

US 2005/0192663 A1    Sep. 1, 2005

Related U.S. Application Data

(60) Division of application No. 10/427,514, filed on May 1, 2003, now Pat. No. 6,908,479, which is a division of application No. 09/779,078, filed on Feb. 8, 2001, now Pat. No. 6,596,022, which is a division of application No. 09/561,098, filed on Apr. 28, 2000, now Pat. No. 6,309,412, which is a division of application No. 09/135,222, filed on Aug. 17, 1998, now Pat. No. 6,056,776, which is a division of application No. 09/055,582, filed on Apr. 6, 1998, now Pat. No. 6,066,168, which is a division of application No. 08/783,097, filed on Jan. 14, 1997, now Pat. No. 5,735,893, which is a division of application No. 08/556,516, filed on Nov. 13, 1995, now Pat. No. 5,603,721, which is a division of application No. 08/281,790, filed on Jul. 28, 1994, now Pat. No. 5,514,154, which is a continuation-in-part of application No. 08/164,986, filed on Dec. 9, 1993, now abandoned, which is a continuation of application No. 07/783,558, filed on Oct. 28, 1991, now abandoned.

(51) Int. Cl.
*A61F 2/06* (2006.01)
*B23P 13/04* (2006.01)
(52) U.S. Cl. ........................................ 623/1.15; 29/557
(58) Field of Classification Search ....... 623/1.11–1.16; 606/198; 29/557
See application file for complete search history.

(56) References Cited

U.S. PATENT DOCUMENTS 2,701,559 A    2/1955    Cooper (Continued)

FOREIGN PATENT DOCUMENTS

AU    A-23784/88    4/1989

(Continued)

OTHER PUBLICATIONS

U.S. Appl. No. 08/630,787, filed Apr. 10, 1996.

(Continued)

*Primary Examiner*—Suzette J Gherbi
(74) *Attorney, Agent, or Firm*—Fulwider Patton LLP

(57) ABSTRACT

The invention is directed to an expandable stent for implantation in a body lumen, such as an artery, and a method for making it from a single length of tubing. The stent consists of a plurality of radially expandable cylindrical elements generally aligned on a common axis and interconnected by one or more interconnective elements. The individual radially expandable cylindrical elements consist of ribbon-like material disposed in an undulating pattern. Portions of the expanded stent project outwardly into engagement with the vessel wall to more securely attach the stent.

5 Claims, 4 Drawing Sheets

U.S. PATENT DOCUMENTS

| | | |
|---|---|---|
| 3,105,492 A | 10/1963 | Jeckel |
| 3,657,744 A | 4/1972 | Ersek |
| 3,868,956 A | 3/1975 | Alfidi et al. |
| 3,993,078 A | 11/1976 | Bergentz et al. |
| 4,130,904 A | 12/1978 | Whalen |
| 4,140,126 A | 2/1979 | Choudhyry |
| 4,159,719 A | 7/1979 | Haerr |
| 4,241,146 A | 12/1980 | Sivachenko et al. |
| 4,323,071 A | 4/1982 | Simpson et al. |
| 4,387,952 A | 6/1983 | Slusher |
| 4,503,569 A | 3/1985 | Dotter |
| 4,504,354 A | 3/1985 | George et al. |
| 4,512,338 A | 4/1985 | Balko et al. |
| 4,516,972 A | 5/1985 | Samson |
| 4,531,933 A | 7/1985 | Norton et al. |
| 4,553,545 A | 11/1985 | Maass et al. |
| 4,560,374 A | 12/1985 | Hammerslag |
| 4,580,568 A | 4/1986 | Gianturco |
| 4,616,652 A | 10/1986 | Simpson |
| 4,619,246 A | 10/1986 | Molgaard-Nielsen et al. |
| 4,649,922 A | 3/1987 | Wiktor |
| 4,650,466 A | 3/1987 | Luther |
| 4,655,771 A | 4/1987 | Wallsten |
| 4,665,906 A | 5/1987 | Jervis |
| 4,665,918 A | 5/1987 | Garza et al. |
| 4,681,110 A | 7/1987 | Wiktor |
| 4,706,671 A | 11/1987 | Weinrib |
| 4,725,334 A | 2/1988 | Brimm |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,760,849 A | 8/1988 | Kropf |
| 4,762,128 A | 8/1988 | Rosenbluth |
| 4,767,418 A | 8/1988 | Deininter |
| 4,768,507 A | 9/1988 | Fischell et al. |
| 4,776,337 A | 10/1988 | Palmaz |
| 4,795,458 A | 1/1989 | Regan |
| 4,800,882 A | 1/1989 | Gianturco |
| 4,830,003 A | 5/1989 | Wolff et al. |
| 4,848,343 A | 7/1989 | Wallsten et al. |
| 4,856,516 A | 8/1989 | Hillstead |
| 4,870,966 A | 10/1989 | Dellon et al. |
| 4,877,030 A | 10/1989 | Beck et al. |
| 4,878,906 A | 11/1989 | Lindemann et al. |
| 4,886,062 A | 12/1989 | Wiktor |
| 4,887,997 A | 12/1989 | Okada |
| 4,892,539 A | 1/1990 | Koch |
| 4,893,623 A | 1/1990 | Rosenbluth |
| 4,907,336 A | 3/1990 | Gianturco |
| 4,913,141 A | 4/1990 | Hillstead |
| 4,921,479 A | 5/1990 | Grayzel |
| 4,922,905 A | 5/1990 | Strecker |
| 4,923,464 A | 5/1990 | DiPisa, Jr. |
| 4,943,346 A | 7/1990 | Mattelin |
| 4,950,227 A | 8/1990 | Savin et al. |
| 4,963,022 A | 10/1990 | Sommargren |
| 4,969,458 A | 11/1990 | Wiktor |
| 4,969,890 A | 11/1990 | Sugita et al. |
| 4,986,831 A | 1/1991 | King et al. |
| 4,988,356 A | 1/1991 | Crittenden et al. |
| 4,990,155 A | 2/1991 | Wilkoff |
| 4,994,071 A | 2/1991 | MacGregor |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Gianturco et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,059,211 A | 10/1991 | Stack et al. |
| 5,061,273 A | 10/1991 | Yock |
| 5,061,275 A | 10/1991 | Wallsten et al. |
| 5,062,829 A | 11/1991 | Pryor et al. |
| 5,064,435 A | 11/1991 | Porter |
| 5,067,957 A | 11/1991 | Jervis |
| 5,071,407 A | 12/1991 | Termin et al. |
| 5,073,694 A | 12/1991 | Tessier et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,089,006 A | 2/1992 | Stiles |
| 5,092,877 A | 3/1992 | Pinchuk |
| 5,100,429 A | 3/1992 | Sinofsly et al. |
| 5,102,417 A | 4/1992 | Palmaz |
| 5,104,404 A | 4/1992 | Wolff |
| 5,108,416 A | 4/1992 | Ryan et al. |
| 5,108,417 A | 4/1992 | Sawyer |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,158,548 A | 10/1992 | Lau et al. |
| 5,161,547 A | 11/1992 | Tower |
| 5,163,952 A | 11/1992 | Froix |
| 5,163,958 A | 11/1992 | Pinchuk |
| 5,171,262 A | 12/1992 | MacGregor |
| 5,180,368 A | 1/1993 | Garrison |
| 5,183,085 A | 2/1993 | Timmermans |
| 5,192,297 A | 3/1993 | Hull |
| 5,192,307 A | 3/1993 | Wall |
| 5,192,311 A | 3/1993 | King et al. |
| 5,195,984 A | 3/1993 | Schatz |
| 5,197,978 A | 3/1993 | Hess |
| 5,217,482 A | 6/1993 | Keith |
| 5,222,971 A | 6/1993 | Willard et al. |
| 5,226,913 A | 7/1993 | Pinchuk |
| 5,234,456 A | 8/1993 | Silverstini |
| 5,242,397 A | 9/1993 | Barath et al. |
| 5,242,399 A | 9/1993 | Lau et al. |
| 5,242,452 A | 9/1993 | Inoue |
| 5,282,823 A | 2/1994 | Schwartz et al. |
| 5,282,824 A | 2/1994 | Gianturco |
| 5,290,295 A | 3/1994 | Querals et al. |
| 5,290,305 A | 3/1994 | Inoue |
| 5,292,331 A | 3/1994 | Boneau |
| 5,304,200 A | 4/1994 | Spaulding |
| 5,314,444 A | 5/1994 | Gianturco |
| 5,314,472 A | 5/1994 | Fontaine |
| 5,330,500 A | 7/1994 | Song |
| 5,344,425 A | 9/1994 | Sawyer |
| 5,344,426 A | 9/1994 | Lau et al. |
| 5,354,308 A | 10/1994 | Simon et al. |
| 5,356,433 A | 10/1994 | Rowland et al. |
| 5,360,401 A | 11/1994 | Turnlund |
| 5,368,566 A | 11/1994 | Crocker |
| 5,372,600 A | 12/1994 | Beyar et al. |
| 5,378,239 A | 1/1995 | Termin et al. |
| 5,383,892 A | 1/1995 | Cardon et al. |
| 5,395,390 A | 3/1995 | Simon et al. |
| 5,405,378 A | 4/1995 | Strecker |
| 5,413,597 A | 5/1995 | Krajicek |
| 5,421,955 A | 6/1995 | Lau |
| 5,423,745 A | 6/1995 | Todd et al. |

| | | | | | | |
|---|---|---|---|---|---|---|
| 5,423,885 | A | 6/1995 | Williams | 6,273,901 B1 | 8/2001 | Whitcher et al. |
| 5,445,646 | A | 8/1995 | Euteneuer et al. | 6,273,910 B1 | 8/2001 | Limon |
| 5,449,373 | A | 9/1995 | Pinchasik | 6,273,911 B1 | 8/2001 | Cox |
| 5,456,694 | A | 10/1995 | Marin et al. | 6,287,336 B1 | 9/2001 | Globerman et al. |
| 5,458,615 | A | 10/1995 | Klemm et al. | 6,340,366 B2 | 1/2002 | Wijay |
| 5,476,476 | A | 12/1995 | Hillstead | 6,344,055 B1 | 2/2002 | Shukov |
| 5,476,506 | A | 12/1995 | Lunn et al. | 6,468,302 B2 | 10/2002 | Cox et al. |
| 5,484,449 | A | 1/1996 | Amundson et al. | 6,852,124 B2 | 2/2005 | Cox et al. |
| 5,507,768 | A | 4/1996 | Lau et al. | 2001/0029397 A1 | 10/2001 | Thompson |
| 5,514,154 | A | 5/1996 | Lau et al. | 2001/0041929 A1 | 11/2001 | Von Oepen |
| 5,527,324 | A | 6/1996 | Krantz et al. | 2002/0007212 A1 | 1/2002 | Brown et al. |
| 5,545,132 | A | 8/1996 | Fagan et al. | | | |
| 5,569,295 | A * | 10/1996 | Lam ........................... 606/198 | | | |
| 5,571,135 | A | 11/1996 | Fraser et al. | | | |

FOREIGN PATENT DOCUMENTS

| | | |
|---|---|---|
| AU | B-61333/90 | 2/1991 |
| AU | B53198/94 | 3/1994 |
| AU | B-53198/94 | 3/1994 |
| CH | 513567 | 11/1971 |
| DE | 2001535 | 7/1970 |
| DE | 1665771 | 1/1971 |
| DE | 2301075 | 7/1973 |
| DE | 2410933 | 9/1974 |
| DE | 118673 | 3/1976 |
| DE | 2708945 | 9/1978 |
| DE | 2920223 | 11/1980 |
| DE | 3205942 | 9/1983 |
| DE | 3516862 | 11/1986 |
| DE | 36 40 745 A1 | 6/1987 |
| DE | 3640745 | 6/1987 |
| DE | 3722749 | 1/1988 |
| DE | 38 23 060 A1 | 1/1989 |
| DE | 3823060 | 1/1989 |
| DE | 3724479 | 2/1989 |
| DE | 69029114 | 11/1996 |
| DE | 195 37 872 A1 | 4/1997 |
| DE | 19537872 | 4/1997 |
| EP | 0062300 | 10/1982 |
| EP | 0 201 466 A2 | 4/1986 |
| EP | 0177330 | 4/1986 |
| EP | 0177453 | 4/1986 |
| EP | 0183372 | 6/1986 |
| EP | 0190543 | 8/1986 |
| EP | 0 221 570 A2 | 5/1987 |
| EP | 0221570 | 5/1987 |
| EP | 0256986 | 2/1988 |
| EP | 0274846 | 7/1988 |
| EP | 0282175 | 9/1988 |
| EP | 0 380 668 B1 | 10/1988 |
| EP | 0290138 | 11/1988 |
| EP | 0308512 | 3/1989 |
| EP | 0312852 | 4/1989 |
| EP | 0 338 816 A2 | 10/1989 |
| EP | 0335341 | 10/1989 |
| EP | 0338816 | 10/1989 |
| EP | 0357003 | 3/1990 |
| EP | 0 361 192 A3 | 4/1990 |
| EP | 0 364 787 A1 | 4/1990 |
| EP | 0361192 | 4/1990 |
| EP | 0364787 | 4/1990 |
| EP | 0 372 789 A3 | 6/1990 |
| EP | 0372789 | 6/1990 |
| EP | 0380668 | 8/1990 |
| EP | 0 407 951 A3 | 1/1991 |
| EP | 0 408 245 A1 | 1/1991 |
| EP | 0407951 | 1/1991 |
| EP | 0408245 | 1/1991 |
| EP | 0417928 | 3/1991 |
| EP | 0 421 729 A2 | 4/1991 |
| EP | 0 423 916 A1 | 4/1991 |
| EP | 0421729 | 4/1991 |
| EP | 0423916 | 4/1991 |
| EP | 0 428 479 A1 | 5/1991 |
| EP | 0428471 | 5/1991 |

| | | | |
|---|---|---|---|
| 5,603,721 | A | 2/1997 | Lau et al. |
| 5,626,604 | A | 5/1997 | Cottone et al. |
| 5,653,690 | A | 8/1997 | Booth et al. |
| 5,653,691 | A | 8/1997 | Rupp et al. |
| 5,653,727 | A | 8/1997 | Wiktor |
| 5,693,089 | A | 12/1997 | Inoue |
| 5,716,393 | A | 2/1998 | Lindenberg et al. |
| 5,716,396 | A | 2/1998 | Williams |
| 5,720,726 | A | 2/1998 | Marcadis et al. |
| 5,733,303 | A | 3/1998 | Israel |
| 5,733,325 | A | 3/1998 | Robinson |
| 5,741,327 | A | 4/1998 | Frantzen |
| 5,746,765 | A | 5/1998 | Kleshinski et al. |
| 5,776,161 | A | 7/1998 | Globerman |
| 5,782,855 | A | 7/1998 | Lau et al. |
| 5,800,521 | A | 9/1998 | Orth |
| 5,800,526 | A | 9/1998 | Anderson et al. |
| 5,810,868 | A | 9/1998 | Lashinski et al. |
| 5,810,871 | A | 9/1998 | Tuckey et al. |
| 5,817,152 | A | 10/1998 | Birdsall |
| 5,827,321 | A | 10/1998 | Roubin et al. |
| 5,830,217 | A | 11/1998 | Ryan |
| 5,836,965 | A | 11/1998 | Jendersee et al. |
| 5,836,966 | A | 11/1998 | St. Germain |
| 5,855,600 | A | 1/1999 | Alt |
| 5,861,027 | A | 1/1999 | Trap |
| 5,902,332 | A | 5/1999 | Schatz |
| 5,906,640 | A | 5/1999 | Penn et al. |
| 5,911,754 | A | 6/1999 | Kanesaka et al. |
| 5,922,021 | A | 7/1999 | Jang |
| 5,925,061 | A | 7/1999 | Ogi et al. |
| 5,938,697 | A | 8/1999 | Killion et al. |
| 5,948,016 | A | 9/1999 | Jang |
| 5,954,743 | A | 9/1999 | Jang |
| 5,980,552 | A | 11/1999 | Pinchasik et al. |
| 5,984,964 | A | 11/1999 | Roberts et al. |
| 5,997,468 | A | 12/1999 | Wolff et al. |
| 6,010,530 | A | 1/2000 | Goicoechea |
| 6,017,365 | A | 1/2000 | Von Oepen |
| 6,030,413 | A | 2/2000 | Lazarus |
| 6,033,435 | A | 3/2000 | Penn et al. |
| 6,042,597 | A | 3/2000 | Kveen et al. |
| 6,042,606 | A | 3/2000 | Frantzen |
| 6,048,361 | A | 4/2000 | Von Oepen |
| 6,059,822 | A | 5/2000 | Kanesaka et al. |
| 6,066,167 | A | 5/2000 | Lau et al. |
| 6,066,168 | A | 5/2000 | Lau et al. |
| 6,071,298 | A | 6/2000 | Lashinski et al. |
| 6,071,308 | A | 6/2000 | Ballou et al. |
| 6,106,548 | A | 8/2000 | Roubin et al. |
| 6,146,358 | A | 11/2000 | Rowe |
| 6,146,403 | A | 11/2000 | St. Germain |
| 6,159,238 | A | 12/2000 | Killion et al. |
| 6,179,867 | B1 | 1/2001 | Cox |
| 6,183,506 | B1 | 2/2001 | Penn et al. |
| 6,200,337 | B1 | 3/2001 | Moriuchi et al. |
| 6,206,910 | B1 | 3/2001 | Berry et al. |
| 6,217,608 | B1 | 4/2001 | Penn et al. |
| 6,231,598 | B1 | 5/2001 | Berry et al. |

| | | |
|---|---|---|
| EP | 0428479 | 5/1991 |
| EP | 0483372 | 5/1992 |
| EP | 0 517 075 A1 | 9/1992 |
| EP | 0 062 300 A2 | 10/1992 |
| EP | 0517075 | 12/1992 |
| EP | 0 540 290 A2 | 5/1993 |
| EP | 0 540 290 B1 | 5/1993 |
| EP | 0 541 443 A1 | 5/1993 |
| EP | 0 541 443 A2 | 5/1993 |
| EP | 0540290 A2 | 5/1993 |
| EP | 0541443 | 5/1993 |
| EP | 0 606 165 A1 | 7/1994 |
| EP | 0 688 545 A1 | 12/1995 |
| EP | 0729767 | 9/1996 |
| EP | 0 417 928 B1 | 11/1996 |
| EP | 0417928 | 12/1996 |
| EP | 0 800 801 A1 | 10/1997 |
| FR | 1571240 | 6/1969 |
| FR | 2476524 | 8/1981 |
| FR | 2 677 872 A1 | 12/1992 |
| FR | 2677872 | 12/1992 |
| GB | 1205743 | 9/1970 |
| GB | 1583192 | 1/1981 |
| GB | 2 070 490 A | 9/1981 |
| GB | 2070490 | 9/1981 |
| GB | 2092894 | 8/1982 |
| GB | 2135585 | 11/1983 |
| GB | 2 135 585 A | 9/1984 |
| JP | 58-501458 | 9/1983 |
| JP | 60-500520 | 4/1985 |
| JP | 61-41444 | 2/1986 |
| JP | 62-213762 | 9/1987 |
| JP | 62-231657 | 10/1987 |
| JP | 62-235496 | 10/1987 |
| JP | 62-235496 A | 10/1987 |
| JP | 62235496 A | 10/1987 |
| JP | 63-214264 | 9/1988 |
| JP | 63-246178 | 10/1988 |
| JP | 63-289990 | 11/1988 |
| JP | 64-83685 | 3/1989 |
| JP | 64-83685 A | 3/1989 |
| JP | 1-145076 | 6/1989 |
| JP | 1-299550 | 12/1989 |
| JP | 2-174859 | 7/1990 |
| JP | 2-255157 | 10/1990 |
| JP | 3-9745 | 1/1991 |
| JP | 3-9745 A | 1/1991 |
| JP | 3-9746 | 1/1991 |
| JP | 3-9746 A | 1/1991 |
| JP | 3-57465 | 3/1991 |
| JP | 3-151983 | 6/1991 |
| JP | 4-25755 | 2/1992 |
| JP | 5-267998 | 10/1993 |
| LU | 79208 | 10/1979 |
| SU | 660689 | 5/1979 |
| SU | 764684 | 9/1980 |
| SU | 1084091 | 4/1984 |
| SU | 1217402 | 3/1986 |
| SU | 1457921 | 2/1989 |
| WO | WO 83/03752 | 11/1983 |
| WO | WO 83/03752 A1 | 11/1983 |
| WO | WO 84/00121 | 1/1984 |
| WO | WO 89/01798 | 3/1989 |
| WO | WO 89/01798 A1 | 3/1989 |
| WO | WO 89/08433 | 9/1989 |
| WO | WO 89/08433 A1 | 9/1989 |
| WO | WO 91/07139 | 5/1991 |
| WO | WO 91/07139 A1 | 5/1991 |
| WO | WO 91/17720 | 11/1991 |
| WO | WO 92/06734 | 4/1992 |
| WO | WO 92/06734 A1 | 4/1992 |
| WO | WO 92/09246 | 6/1992 |
| WO | WO 92/09246 A1 | 6/1992 |
| WO | WO 94/17754 | 8/1994 |
| WO | WO 94/17754 A1 | 8/1994 |
| WO | WO 95/23563 | 9/1995 |
| WO | WO 95/23563 A1 | 9/1995 |
| WO | WO 95/26695 | 10/1995 |
| WO | WO 95/26695 A2 | 10/1995 |
| WO | WO 96/09013 | 3/1996 |
| WO | WO 96/09013 A1 | 3/1996 |
| WO | WO 96/26689 | 9/1996 |
| WO | WO 96/26689 A1 | 9/1996 |
| WO | WO 98/22159 | 5/1998 |
| WO | WO 98/22159 A2 | 5/1998 |
| WO | WO 98/48734 | 11/1998 |
| WO | WO 98/48734 A1 | 11/1998 |
| WO | WO 99/02105 | 1/1999 |
| WO | WO 99/02105 A1 | 1/1999 |

OTHER PUBLICATIONS

U.S. Appl. No. 08/943,992, filed Oct. 3, 1997.
Vascular's Opening Claim Construction Brief for the Lau Patents, *ACS v. AVE*, 98-80-SLR (D. Del.) (Aug. 13, 2004).
Plaintiff's Answering Claim Construction Brief Regarding Lau Patent Terms, *ACS v. AVE*, 98-80-SLR (D. Del.) (Sep. 24, 2004).
Memorandum Opinion Granting ACS's Motion for Summary Judgement That Michael D. Boneau is Not an Inventor of the Lau Patents and That the Lau Patents are Not Invalid Under 35 U.S.C. § 102(f), *ACS v. AVE*, 98-80-SLR (D. Del.) (Jan. 5, 2005).
Memorandum Order Defining Lau Patent Terms, *ACS v. AVE*, 98-80-SLR (D. Del.) (Jan. 5, 2005).
Notice of Medtronic Vascular, Inc. to Advanced Cardiovascular Systems, Inc. and Guidant Sales Corporation Pursuant to 35 U.S.C. § 282, *ACS v. AVE*, 98-80-SLR (D. Del.) (Jan. 10, 2005).
Trial Transcript (Liability), vol. A, *ACS v. AVE*, 98-80-SLR (D. Del.) (Feb. 7, 2005).
Trial Transcript (Liability), vol. B, *ACS v. AVE*, 98-80-SLR (D. Del.) (Feb. 8, 2005).
Trial Transcript (Liability), vol. C, *ACS v. AVE*, 98-80-SLR (D. Del.) (Feb. 9, 2005).
Trial Transcript (Liability), vol. D, *ACS v. AVE*, 98-80-SLR (D. Del.) (Feb. 10, 2005).
Trial Transcript (Liability), vol. E, *ACS v. AVE*, 98-80-SLR (D. Del.) (Feb. 11, 2005).
Medtronic's Corrected Motion for Judgement as a Matter of Law, *ACS v. AVE*, 98-80-SLR (D. Del.) (Feb. 11, 2005).
ACS's Opposition to Medtronic's Motion for Judgement as a Matter of Law on Infringement, *ACS v. AVE*, 98-80-SLR (D. Del.) (Feb. 14, 2005).
Trial Transcript (Liability), vol. F, *ACS v. AVE*, 98-80-SLR (D. Del.) (Feb. 15, 2005).
Trial Transcript (Liability), vol. G, *ACS v. AVE*, 98-80-SLR (D. Del.) (Feb. 16, 2005).
ACS's Motion for Judgement as a Matter of Law That The '154, '167, '168 and '133 Patents are (1) Not Invalid as Anticipated, (2) Not Invalid Under 35 U.S.C. § 112, and (3) Not Invalid as Obvious, *ACS v. AVE*, 98-80-SLR (D. Del.) (Feb. 16, 2005).
ACS's Motion for Judgement as a Matter of Law That the Accused Medtronic Products Infringe the Asserted Claims of the Lau Patents-in-Suit, *ACS v. AVE*, 98-80-SLR (D. Del.) (Feb. 16, 2005).
Trial Transcript (Liability), vol. H, *ACS v. AVE*, 98-80-SLR (D. Del.) (Feb. 17, 2005).
Trial Transcript (Liability), vol. I, *ACS v. AVE*, 98-80-SLR (D. Del.) (Feb. 18, 2005).
Jury Verdict, *ACS v. AVE*, 98-80-SLR (D. Del.) (Feb. 18, 2005).
Medtronic's Renewed Motion for Judgement as a Matter of Law, *ACS v. AVE*, 98-80-SLR (D. Del.) (Apr. 18, 2005).
Trial Transcript (Inequitable Conduct), *ACS v. AVE*, 98-80-SLR (D. Del.) (Jun. 7, 2005).
Trial Transcript (Inequitable Conduct), *ACS v. AVE*, 98-80-SLR (D. Del.) (Jun. 8, 2005).
ACS's Response to Medtronic's Renewed Motion for Judgment as a Matter of Law, *ACS v. AVE*, 98-80-SLR (D. Del.) (Jun. 17, 2005).

Medtronic's Reply Brief in Support of Its Motion for Judgment as a Matter of Law, *ACS* v. *AVE*, 98-80-SLR (D. Del.) (Jul. 18, 2005).
Medtronic's Opening Post-Trial Brief on ACS's Inequitable Conduct Before the U.S. Patent and Trademark Office, *ACS* v. *AVE*, 98-80-SLR (D. Del.) (Jul. 28, 2005).
ACS's Post Trial Brief in Response to Medtronic's Allegations of Inequitable Conduct, *ACS* v. *AVE*, 98-80-SLR (D. Del.) (Sep. 19, 2005).
Medtronic's Reply Post-Trial Brief on ACS's Inequitable Conduct Before the U.S. Patent and Trademark Office, *ACS* v. *AVE*, 98-80-SLR (D. Del.) (Oct. 7, 2005).
Docket, *ACS* v. *SciMed*, 98-1108 (S.D. Indiana) (Undated).
Memorandum of Law In Support of Plaintiff's Proposed Construction of Patent Claims, *ACS* v. *SciMed*, 98-1108 (S.D. Indiana) (Jul. 29, 1999).
Defendant's Pre-Markman Hearing Memorandum on Claim Construction, *ACS* v. *SciMed*, 98-1108 (S.D. Indiana) (Jul. 29, 1999).
Defendant's Memorandum in Opposition to Plaintiffs' Proposed Construction of Patent Claims, *ACS* v. *SciMed*, 98-1108 (S.D. Indiana) (Aug. 12, 1999).
Memorandum of Law in Reply to Defendants' Pre-Markman Hearing Memorandum on Claim Construction, *ACS* v. *SciMed*, 98-1108 (S.D. Indiana) (Aug. 12, 1999).
Expert Witness Report of John F. Witherspoon, *ACS* v. *SciMed*, 98-1108 (S.D. Indiana) (Sep. 27, 1999).
Expert Report of Dr. David Cumberland, *ACS* v. *SciMed*, 98-1108 (S.D. Indiana) (Sep. 27, 1999).
Entry on Claim Construction Issues, *ACS* v. *SciMed*, 98-1108 (S.D. Indiana) (Oct. 15, 1999).
Supplemental Expert Report of Dr. C. Forbes Dewey, Jr.,*ACS* v. *SciMed*, 98-1108 (S.D. Indiana) (Nov. 12, 1999).
Memorandum in Support of Defendants' Motion for Additional Findings on Certain Claim Construction Issues and Reconsideration of One Issue,*ACS* v. *SciMed*, 98-1108 (S.D. Indiana) (Nov. 19, 1999).
Supplement to Defendants' Memorandum in Support of Their Motion for Addition Findings on Claim Construction Issues and Reconsideration of One Issue, *ACS* v. *SciMed*, 98-1108 (S.D. Indiana) (Dec. 1, 1999).
Memorandum of Law in Opposition to Defendants' Motion for Additional Findings on Claim Construction Issues and Reconsideration of One Issue, *ACS* v. *SciMed*, 98-1108 (S.D. Indiana) (Dec. 6, 1999).
Reply Memorandum in Support of Defendants' Motion for Additional Findings on Claim Construction Issues and Reconsideration of One Issue, *ACS* v. *SciMed*, 98-1108 (S.D. Indiana) (Dec. 15, 1999).
Memorandum of Law in Support of Guidant/ACS's Motion for Partial Summary Judgment Against Defendants' Affirmative Defense of Inequitable Conduct in Obtaining the Patents in Suit, *ACS* v. *SciMed*, 98-1108 (S.D. Indiana) (Dec. 15, 1999).
Defendants Notice to the Court that the Issue Raised by Plaintiffs' Motion for Partial Summary Judgment Regarding Inventorship by Michael Boneau is Moot, *ACS* v. *SciMed*, 98-1108 (S.D. Indiana) (Dec. 22, 1999).
Reply Memorandum of Law in Further Support of Plaintiffs' Motion for Partial Summary Judgement Against Defendants' Affirmative Defense of Inequitable Conduct Concerning Michael Boneau, *ACS* v. *SciMed*, 98-1108 (S.D. Indiana) (Dec. 29, 1999).
Defendants SciMed Life Systems, Inc. and Boston Scientific Corporation's Notice Pursuant to 35 U.S.C. § 282, *ACS* v. *SciMed*, 98-1108 (S.D. Indiana) (Jan. 21, 2000).
Order, *ACS* v. *SciMed*, 98-1108 (S.D. Indiana) (Feb. 9, 2000).
Entry on Plaintiff's Motion for Partial Summary Judgment on Defendants' Affirmative Defense of Inequitable Conduct in Obtaining the Patents in Suit, *ACS* v. *SciMed*, 98-1108 (S.D. Indiana) (Feb. 9, 2000).
Entry on Defendants' Motion for Supplemental Claim Construction, *ACS* v. *SciMed*, 98-1108 (S.D. Indiana) (Feb. 9, 2000).
Motion to Withdraw Defendants' Motion for Summary Judgment of Invalidity, *ACS* v. *SciMed*, 98-1108 (S.D. Indiana) (May 18, 2000).
Order Granting Motion to Withdraw Defendants' Motion for Summary Judgment of Invalidity, *ACS* v. *SciMed*, 98-1108 (S.D. Indiana) (May 19, 2000).
Brief for Plaintiffs-Appellants Advanced Cardiovascular Systems, Inc. and Guidant Sales Corporation, *ACS* v. *SciMed*, Appeal No. 00-1454 (Fed. Cir.) (Sep. 1, 2000).
Brief for Defendants-Appellees SciMed Life Systems, Inc. and Boston Scientific Corporation, *ACS* v. *SciMed*, Appeal No. 00-1454 (Fed. Cir.) (Oct. 30, 2000).
Reply Brief for Plaintiffs-Appellants Advanced Cardiovascular Systems, Inc. and Guidant Sales Corporation, *ACS* v. *SciMed*, Appeal No. 00-1454 (Fed. Cir.) (Nov. 29, 2000).
Decision, *ACS* v. *SciMed*, Appeal No. 00-1454 (Fed. Cir.) (Aug. 6, 2001).
Notice of Opposition, EP 0 807 424 Opposition Proceedings (Apr. 21, 2000).
Notice of Opposition, EP 0 807 424 Opposition Proceedings (May 3, 2000).
Response to Notices of Opposition, EP 0 807 424 Opposition Proceedings Feb. 7, 2001).
Reply to Response to Notices of Oppositions, EP 0 807 424 Opposition Proceedings (Jun. 18, 2001).
Remarks Regarding Response to Opposition, EP 0 807 424 Opposition Proceedings May 16, 2002).
Response to Remarks Regarding Response to Opposition, EP 0 807 424 Opposition Proceedings (May 17, 2002).
Facts and Submissions (Grounds for Decision), EP 0 807 424 Opposition Proceedings (Jul. 4, 2002).
Minutes of oral proceedings and decision with corresponding documents, EP 0 807 424 Opposition Proceedings (Jul. 18, 2002).
Notice of Opposition, EP 0 807 424 Opposition Proceedings (Aug. 19, 2002).
Notice of Appeal, EP 0 807 424 Opposition Proceedings (Sep. 17, 2002).
Submission regarding Grounds of Appeal, EP 0 807 424 Opposition Proceedings (Nov. 28, 2002).
Claims, EP 0 807 424 Opposition Proceedings (Nov. 29, 2002).
Response to Submission Requesting Appeal, EP 0 807 424 Opposition Proceedings (Jun. 16, 2003).
Preliminary Assessment of Appeal by Technical Board of Appeal, EP 0 807 424 Opposition Proceedings (Jan. 30, 2004).
Response to Preliminary Assessment of Appeal by Technical Board of Appeal by Opponent, EP 0 807 424 Opposition Proceedings (Jun. 1, 2004).
Response to Preliminary Assessment of Appeal by Technical Board of Appeal by Patentee, EP 0 807 424 Opposition Proceedings (Jun. 7, 2004).
Minutes of oral proceedings and decision of Technical Board of Appeal, EP 0 807 424 Opposition Proceedings (Jul. 8, 2004).
Notification of decision, EP 0 807 424 Opposition Proceedings (Aug. 12, 2004).
Maintenance of the Patent with the Documents Specified in the Final Decision, EP 0 807 424 Opposition Proceedings (Aug. 20, 2004).
Decision to Maintain the European Patent in Amended Form, EP 0 807 424 Opposition Proceedings (Dec. 15, 2004).
Termination of the opposition proceedings with maintenance of patent (Jan. 28, 2005).
Notice of Opposition, EP 0 504 290 Opposition Proceedings (Oct. 22, 1998).
Notice of Opposition, EP 0 504 290 Opposition Proceedings (Oct. 23, 1998).
Letter enclosing new citation to Oct. 23, 1998 Opposition by Terumo, EP 0 504 290 Opposition Proceedings (Dec. 21, 1998).
Reply of Patent Proprietor to Notices of Opposition, EP 0 504 290 Opposition Proceedings (Jun. 14, 1999).
Letter Responding to Patentee's Jun. 14, 1999 Letter by Opponent Dr. Schmiedl with Attachments, EP 0 504 290 Opposition Proceedings (Oct. 18, 1999).
Reply to DOBS by Novis Srl, EP 0 504 290 Opposition Proceedings (Jan. 5, 2000).
Letter from Proprietor enclosing Declaration of Gary Schniederman and First Auxiliary Request, EP 0 504 290 Opposition Proceedings (Aug. 17, 2000).
Minutes of Oral Proceedings and Decision, EP 0 504 290 Opposition Proceedings (Oct. 24, 2000).
Claims, EP 0 504 290 Opposition Proceedings (Oct. 24, 2000).
Opposition Divisions' Decision revoking EP '290, EP 0 504 290 Opposition Proceedings (Oct. 24, 2000).

Statements of Grounds of Appeal, EP 0 504 290 Opposition Proceedings (Mar. 2, 2001).

Schmiedl's Submission in Answer to Appeal, EP 0 504 290 Opposition Proceedings (Jun. 27, 2001).

Novis Srl's Request that Appeal be Rejected, EP 0 504 290 Opposition Proceedings (Aug. 17, 2001).

Terumo's Response to Patentee's Appeal, EP 0 504 290 Opposition Proceedings (Sep. 12, 2001).

Withdrawal of Opposition by Dr. Schmiedl, EP 0 504 290 Opposition Proceedings (Oct. 15, 2001).

Letter from Patentee Amending Main Request, EP 0 504 290 Opposition Proceedings (May 30, 2003).

Minutes of Oral Proceedings and Decision, EP 0 504 290 Opposition Proceedings (Jul. 10, 2003).

Notification of Decision and Appeal Board Decision, May 30, 2003 (Sep. 18, 2003).

Termination of the Opposition Proceedings with the Revocation of Patent, May 30, 2003 (Sep. 23, 2003).

Medtronic's Motion for New Trial Pursuant to Fed.R.Civ.59(a), *ACS v. Medtronic Vascular, Inc.*, 98-80-SLR (D. Del.) (Apr. 18, 2005).

ACS's Response to Medtronic's Motion for New Trial Pursuant to Fed. R. Civ. P. 59(a), *ACS v. Medtronic Vascular Inc.*, 98-80-SLR (D. Del.) (Jun. 17, 2005).

Medtronic's Reply Brief in support of its Motion for New Trial Pursuant to Fed.R.Civ.P.59(a), 98-80-SLR (D. Del.) (Jul. 18, 2005).

Alvarado, R., et al., "Evaluation of Polymer-Coated Balloon-Expandable Stents in Bile Ducts," *Radiology*, 170, 3: 975-978, Mar. 1989.

American Heart Association 61st Scientific Sessions, Abstract Form. "A New Percutaneous Expandable Stent."

Baier, R., et al., "Initial Events in Interaction of Blood with a Foreign Surface," *Journal of Biomedical Material Research*, 3: 191-206, 1969.

Balko, A., et al., "Transfemoral Placement of Intraluminal Polyurethane Prosthesis for Abdominal Aortic Aneurysm," *Journal of Surgical Research*, 40: 305-309, 1986.

Becker, G., et al., "Early Experience with the Palmaz Stent in Human Iliac Angioplasty," *Indiana Medicine*, 286-292, Apr. 1989.

Becker, G., et al., "Simultaneous Angioplasty and Intraluminal Grafting with the Palmaz Expandable Intraluminal Graft," 72nd *Scientific Assembly and Annual Meeting of the Radiological Society of North America*, Chicago, Nov./Dec. 1986.

Bonzel, T., et al., "The Sliding Rail System (Monorail): Description of a New Technique for Intravascular Instrumentation and its Application to Coronary Angioplasty," *Kardologie*, Supplement 6: 119-122, 1987.

Brochure: "Anomatic II Positioning Controller," printed by Anorad Corporation.

Campbell, C., et al., "Expanded Microporous Polytetrafluoroethylene as a Vascular Substitute: A Two Year Follow-up," *Surgery*, No. 2: 177-183, Feb. 1979.

Carrasco, C., et al., "Expandable Biliary Endoprosthesis: An Experimental Study," *American Journal of Roentgenology*, 145: 1279-1281, Dec. 1985.

Castaneda-Zuniga, W., ed., Tranluminal Angioplasty, 1983.

Charnsangavej, C., et al., "A New Expandable Metallic Stent for Dilation of Stenotic Tubular Structures: Experimental and Clinical Evaluation," *Houston Medical Journal*, 3, No. 2: 41-51, 1987.

Cimochowski, G., et al., "Greenfield Filter Versus Mobin-Uddin Umbrella," *Journal of Thoracic and Cardiovascular Surgery*, 79, No. 3: 358-365, Mar. 1980.

Coons, H., et al, "Large-Bore, Long Biliary Endoprostheses (Biliary Stents) for Improved Drainage," *Radiology*, 148, No. 1: 89-94, Jul. 1983.

Cope, C., "Balloon Dilatation of Closed Mesocaval Shunts," *American Journal of Roentgenology*, 135: 989-993, Nov. 1980.

Cragg, A., "A New Percutaneous Vena Cava Filter," *American Journal of Roentgenology*, 141: 601-604, Sep. 1983.

Cragg, A., et al., "Percutaneous Arterial Grafting," *Radiology*, 150, No. 1: 45-49, Jan. 1984.

Culverwell, M., "Angioplasty Stents May Prevent Restenosis," *Carcio*, 11-13, Jan. 1987.

Dalessandri, K., et al., "The Effect of Lumbar Sympathectomy on Postsynaptic Vascular Smooth Muscle Response in the Lower Limb in Dogs," *Cardiovascular and Interventional Radiology*, 11: 82-85, 1988.

De Palma, V., et al., "Investigation of Three Surface Properties of Several Metals and their relation to Blood Compatibility," *Journal of Biomedical Materials Research Symposium*, 3: 37-75, 1972.

Denny, D., et al., "Percutaneous Kimray-Greenfield Filter Placement by Femoral Vein Puncture," *American Journal of Roentgenology*, 145: 827-829, Oct. 1985.

Deriu, G., "The Rationale for Patch-Graft Angioplasty After Carotid Endarterectomy: Early and Long-Term Follow-Up," *Stroke*, 15: No. 6 972-979, Nov. 1984.

Dichek, D.A., et al., "Seeding of Intravascular Stents with Genetically Engineered Endothelial Cells," *Circulation*, 80: 1237-1353, 1989.

Dorros, G., et al., "Clinical Research: Angioplasty," *Circulation* (Supplement), 74, No. 1448: II-363, 1986.

Dotter, C., "Interventional Radiology—Review of an Emerging Field," *Seminars in Roentgenology*, 16, No. 1, Jan. 1981.

Dotter, C., et al., "Transluminal Treatment of Arteriosclerotic Obstruction," *Circulation*, 30: 654-670, Nov. 1964.

Duprat, G., et al, "Self-expanding Metallic Stents for Small Vessels: An Experimental Evaluation," *Radiology*, 192: 469-472, 1987.

Flexible Balloon-expanded Stent for Small Vessels, Work in Progress, *Radiology*, 162: 276-278, 1987.

Edwards, W., "Arterial Grafts," *Archives of Surgery*, 113, No. 9: 1225-1233, Nov. 1978.

Eichelter, P., et al., Prophylaxis of Pulmonary Embolism, *Archives of Surgery*, 97: 348-356, Aug. 1968.

Fallone, B., "Elastic Characteristics of the Self-Expanding Metallic Stents," *Investigative Radiology*, 23: 370-376, 1988.

Finci, L., et al., "Percutaneous Transluminal Coronary Angioplasty of Bifurcation Narrowing Using the Kissing Wire Monorail Balloon Technique," *The American Journal of Cardiology*, Apr. 1987.

Fogarty, T., et al., "Adjunctive Intraoperative Arterial Dilation: Simplified Instrumentation Technique," *Archives of Surgery*, 116: 1391-1398, 1981.

Fogarty, T., et al., "Current Status of Dilatation Catheters and Guiding Systems," *American Journal of Cardiology*, 53, No. 12: 97C-100C, Jun. 1984.

Fogarty, T., et al., "Intraoperative Coronary Artery Balloon-Catheter Dilation," *American Heart Journal*, 107, No. 4: 845-851, 1984.

Frimberger, E., "Expanding Spiral—A New Type of Prosthesis for the Palliative Treatment of Malignant Esophageal Stenoses," *Endoscopy*, 15: 213-214, 1983.

Gardner, R., et al., "The Surgical Experience and a One to Sixteen Year Follow-Up of 277 Abdominal Aortic Aneurysms," *American Journal of Surgery*, 135, No. 1: 226-230, Jan. 1978.

Goldstein, H., et al, "Transcatheter Occlusion of Abdominal Tumors," *Radiology*, 120, No. 3: 539-545, Sep. 1976.

Greenfield, L., et al, "A New Intracaval Filter Permitting Continued Flow and Resolution of Emboli," *Surgery*, 73, No. 4: 599-606, Apr. 1973.

Gunther, R., et al, "Percutaneous Nephropyelsotomy Using a Fine-Needle Puncture Set," *Radiology*, 132, No. 1: 228-230, Jul. 1979.

Gunther, R., et al., "Vena Caval Filter to Prevent Pulmonary Embolism: Experimental Study," *Radiology*, 156, No. 2: 315-320, Aug. 1985.

Harries-Jones, E., et al., "Repositioning of Biliary Endoprosthesis with Gruntzig Balloon Catheters," *American Journal of Roentgenology*, 138: 771-772, Apr. 1982.

Harrington, J., et al., "The Palmaz-Schatz Stent," *Handbook of Cardiovascular Interventions/Vascular Interventions*, 536-572.

Hoevels, J., et al., "Percutaneous Transhepatic Insertion of a Permanent Endoprosthesis on Obstructive Lesions of the Extrahepatic Bile Ducts," *Gastrointestinal Radiology*, 4: 367-377, 1979.

Honickman, S., "Malpositioned Biliary Endoprosthesis," *Radiology*, 144: 423-425, Jul. 1982.

Hunter, J., et al., "Experimental Balloon Obstruction of the Inferior Vena Cava," *Annals of Surgery*, 171, No. 2: 315-320, Feb. 1970.

IBM Technical Disclosure Bulletin, Band 11, Nr. 9, Feb. 1969, Seite 1151, New York, US J.F. Smith u.a.: "Selectively removing dielectric materials".

Inoue, K., et al., "Clinical Application of Transvenous Mitral Commissurotomy by a New Balloon Catheter," *Thoracic Cardiovascular Surgery*, 87, No. 3: 394-402, Mar. 1984.

*Journal of the American College of Cardiology* (Supplement A): 106A, (from Abstract of the 36th Annual Scientific Session, American College of Cardiology, New Orleans, Louisiana, Mar. 8-12, 1987), Elsevier (Feb. 1987).

Kaltenbach, M., Abstracts, *Zeitschrift fur Kardiologie*, Apr. 3, 1991 (German only).

Kan, J., et al., "Percutaneous Balloon Valvuloplasty: A New Method for Treating Congenital Pulmonary-Valve Stenosis," *New England Journal of Medicine*, 307, No. 9, 540-542, 1982.

Kerlan, R., et al., "A Simple Method for Insertion of Large Untapered Catheters," *American Journal of Roentgenology*, 141: 792, 1983.

Kerlan, R., et al., "Biliary Endoprostheses: Insertion Using a Combined Peroral-Transhepatic Method," *Radiology*, 150, No. 3: 828-830, 1984.

Lababidi, Z., et al., "Percutaneous Balloon Aortic Valvuloplasty: Results in 23 Patients," *American Journal of Cardiology*, 53: 194-197, Jan. 1984.

Lary, B., et al., "The Experimental Use of Steel Mesh Tubes for Replacement Arterial Segments," *AMA Archives of Surgery*, 72: 69-75, Jan. 1956.

Lawrence, D., et al., "Percanteous Endovascular Graft: Experimental Evaluation," *Radiology*, 163: 357-360, 1987.

Lewandowski, B., et al., "The Air-Filled Hepatic Duct: The Saber Sign as an Aid to the Radiographic Diagnosis Pneumobilia," *Radiology*, 153, No. 2: 329-332, Nov. 1984.

Lund, G., et al., "A New Vena Caval Filter for Percutaneous Placement and Retrieval: Experimental Study," *Radiology*, 152, No. 2: 369-372, Aug. 1984.

Lunderquitst, A., et al., "Guidewire for Percutaneous Transhepatic Cholangiography," *Radiology*, 132, No. 1: 228, Jul. 1979.

Meenaghan, M., et al., "Tissue Response to Surface-Treated Tantalum Implants: Preliminary Observations in Primates," *Biomedical Materials Research*, 13, No. 4: 631-643, Jul. 1979.

Mirich, D., et al., "Percantaneously Placed Endovascular Grafts for Aortic Aneurysms: Feasibility Study," *Radiology*, 170: 1033-1037, 1989.

Mobin_Uddin, K., et al., "The Inferior vena Cava Umbrella Filter," *Progress in Cardiovascular Diseases*, 17, No. 5: 391-399, Mar./Apr. 1975.

Mobin-Uddin, K., et al., "Caval Interruption for Prevention of Pulmonary Embolism," *Archives of Surgery*, 99: 711-715, Dec. 1969.

Muller, D., et al., "Advances in Coronary Angioplasty: Endovascular Stents," *Coronary Artery Disease*, 1: 438, Jul./Aug. 1990.

Mullins, C., et al., "Implantation of Balloon-Expandable Intravascular Grafts by Cathertization in Pulmonary Arteries and Systemic Veins," *Circulation*, 77: 188-189, 1988.

Nanda, R., et al., "Effect of Maxillary Osteotomy on Subsequent Craniofacial Growth in Adolescent Monkeys," *American Journal of Orthod.*, 83: 391-407, May 1983.

Palestrant, Al., et al., "Comparative In Vitro Evaluation of the Nitinol Inferior Vena Cava Filter," *Radiology*, 145: 351-355, Nov. 1982.

Palmaz, J., "Balloon Expandable Intra-Arterial Stents: Effect of Anticoagulation on Thrombus Formation," *Circulation* (Supplement Part II), 76, No. 4: 180, Oct. 1987.

Palmaz, J., "Balloon-Expandable Intravascular Stent," *American Journal of Roentgenology*, 150: 1263-1269, Jun. 1988.

Palmaz, J., "Chapter 30: Overview of Intravascular Stents," in Kim, D., et al., *Peripheral Vascular Imaging and Intervention*, 507-508, 1992.

Palmaz, J., "Die intraluminale Sten-Implantation nach Palmaz," *Radiologe*, 11: 560-563, 1987.

Palmaz, J., "Expandable Intraluminal Vascular Graft: A Feasibility Study," *Surgery*, 2: 199-205, 1986.

Palmaz, J., et al., "Atherosclerotic Rabbit Aortas: Expandable Intraluminal Grafting," *Radiology*, 3: 723-726, 1986.

Palmaz, J., et al., "Balloon Expandable Intraluminal Grafting of Normal and Abnormal Renal Arteries: Experimental Study," $72_{nd}$ *Scientific Assembly and Annual Meeting*, Radiology Society of North America, Chicago, 1-23 [plus figures], Nov. 1986.

Palmaz, J., et al., "Balloon-Expandable Intraarterial Stents: Effect of Antithrombotic Medication on Thrombus Foramtion," *Pros and COns in PTA and Auxiliary Methods*, 170-178, 1989.

Palmaz, J., et al., Early Endothelisation of Balloon-expandable Stents: Experimental Observations, *Journal of Interventional Radiology*, 3: 119-124, 1988.

Palmaz, J., et al., "Expandable Intrahepatic Portacaval Shunt Stents: Early Experience in the Dog," *American Journal of Roentgenology*, 145: 821-825, 1985.

Palmaz, J., et al., "Expandable Intrahepatic Portacaval Shunt Stents in Dogs with Chronic Portal Hypertension," *American Journal of Roentgenology*, 147: 1251-1254, 1986.

Palmaz, J., et al., "Intraluminal Stents in Arterosclerotic Iliac Artery Stenosis: Preliminary Report of Multicenter Study," *Radiology*, 168, No. 3: 727-731, Sep. 1988.

Palmaz, J., et al., "Normal Stenotic Renal Arteries: Experimental Balloon-Expandable Intraluminal Stenting," *Radiology*, 164: 705-708, Sep. 1987.

Palmaz, J., et al., "Removable Biliary Endoprosthesis," *American Journal of Roentgenology*, 140: 812-814, Apr. 1983.

Palmaz, J., Monograph (1980).

Palmaz, J., Monograph (May 18, 1983).

Palmaz, J., *The Current Status of Vascular Prosthesis*, Presentation of The Society of CV & Interventional Radiology' Twelfth Annual Course on *Diagnostic Angiography and Interventional Radiology*, 118-120, Mar. 23-26, 1987.

Papanicolaou, N., et al., "Insertion of a Biliary Endoprosthesis using a Balloon Dilation Catheter," *Gastrointestinal Radiology*, 10: 394-396, 1985.

Pate, J. et al., "A New Form of Venal Caval Interruption," *Annals of Surgery*, 169, No. 6, 873-880, Jun. 1969.

Puel, J., et al., "Intravascular Stents to Prevent Restenosis After Transluminal Coronary Angioplasty," *Circulation* (Supplement Part II), 76, No. 4: 0105, Oct. 1987.

Rashkind, W., et al., "Creation of an Atrial Septal Defect Without Thoracotomy: A Palliative Approach to Complete Transposition of the Great Arteries," *Journal of the American Medical Association*, 196: 173-174, Jun. 1966.

Rees, C., et al., "Angioplasty and Stenting of Completely Occuluded Iliac Arteries," *Radiology* (Part 2), 172, No. 3, 953-959, Sep. 1989.

Rees, C., et al., "DSA in Acute Gastrointestinal Hemorrhage: Clinical and in Vitro Studies," *Radiology*, 169, No. 2: 499-503, Nov. 1988.

Rees, C., et al., "The Hemodynamic Effects of the Administration of Ionic and Nonionic Contrast Materials into the Pulmonary Arteries of a Canine Model of Acute Pulmonary Hypertension," *Investigative Radiology*, 23, No. 3: 184-189, Mar. 1988.

Richter, G., et al., "Der Transjuguslaere Intrahepatische Portosystemische Stent-Shunt (TIPSS); Eine Neue Nichtoperative, Perkutane Methode," *Radiologe*, 29: 406-411, 1989.

Richter, G., et al., "Die Behandlung eines akuten Beckenarterienverschlusses durch Katheterlyse, Katheterdilatation und Implantation einer neuartigen metallischen Gefa.beta.ednoprothese," *Der chirurg*, 60, No. 5: 346-351, May 1989.

Ring, E., et al., "A Simple, Indwelling Biliary Endoprosthesis Made From Common Available Catheter Material," *American Journal of Roentgenology*, 139: 615-617, Sep. 1982.

Roehm, J., et al., "Percutaneous Transcatheter Filter for the Interior Vena Cava," *Radiology*, 150, No. 1: 255-257, Jan. 1984.

Roland, M., Spiral Teflon Stent for Tuboplasty Involving Fimbria, *Obstetrics Gynecology*, 36: 359-362. 1970.

Rollins, N., et al., "Self-expanding Metallic Stents: Preliminary Evaluation in an Atheroschlerotic Model," *Radiology*, 163, No. 3: 739-742, Jun. 1987.

Rosch, J., et al., "Gianturco Expandable Wire Stents in the Treatment of Superior Vena Cava Syndrome Recurring After Maximum-Tolerance Radiation," *Cancer*, 60: 1243-1246, 1987.

Rosch, J., et al., "Modified Gianturco Expandable Wire Stents in Experimental and Clinical Use," *Annales de Radiologie*, 31, No. 2: 100-103, 1987.

Portacaval Shunt: An Experimental Work, *American Journal of Surgery*, 121: 588-592, May 1971.

Roubin, G., et al., "Early and Late Results of Intracoronary Arterial Stenting After Coronary Angioplasty in Dogs," *Circulation*, 4: 891-897, 1987.

Rousseau, H., et al., "Percutaneous Vascular Stent: Experimental Studies and Preliminary Clinical Results in peripheral Arterial Diseases," *Inter. Angio.*, 6: 153-161, 1987.

Rousseau, H., et al., "Self-Expanding Endovascular Prosthesis: An Experimental Study," *Radiology*, 164: 709-714, Sep. 1987.

Saunders, W., "Dorland's Illustrated Medical Dictionary," 675 & 759, *26th Edition, 1981*.

Schatz, R., "Introduction to Intravascular Stents," *Cardiology Clinics*, 6, No. 3: 357-372, 1988.

Schatz, R., et al., "A View of Vascular Stents," *Circulation*, 79: 445-457, 1989.

Schatz, R., et al., "Balloon Expandable Intracoronary Stents in Dogs," *Circulation* (Supplement Part II), 74: II-458, 1824, 1986, 1986.

Schatz, R., et al., "Balloon Expandable Intravascular Grafts," *16th Annual Symposium of the Texas Health Institute—International Symposium on Interventional Cardiology*, Houston, Sep. 1986.

Schatz, R., et al., "Balloon-Expandable Intracoronary Stents in the Adult Dog," *Circulation*, 76, No. 2 450-457, 1987.

Schatz, R., et al., "Intravasacular Stents for Angioplasty," *Cardio*, 27-31, Dec. 1987.

Schatz, R., et al., "New Technology in Angioplasty: Balloon-Expandable Intravascular Stents," *New Developments in Medicine*, 2, No. 2: 59-75, Sep. 1987.

Sechler, E.S., *Elasticity in Engineering*, 1956.

Semb, B., et al., "Balloon Valvulotomy of Congenital Pulmonary Valve Stenosis with Tricuspid Valve Insufficiency," *Cardiovascular Radiology*, 2: 239-241, 1979.

Sigwart, U., et al., "Initial Experience With A New Approach to Stenting of Peripheral and Coronary Arteries."

Sigwart, U., et al., "Intravascular Stents to Prevent Occlusion and Restenosis After Transluminal Angioplasty," *New England Journal of Medicine*, 316: 701-706, 1987.

Sigwart, U., et al., "One Year of Percutaneous Coronary Stenting," *Circulation* (Supplement Part II), 76, No. 4: 0104, Oct. 1987.

Simon, M., et al., "A Vena Cava Filter Using Thermal Shape Memory Alloy," *Radiology*, 125: 89-94, Oct. 1977.

Simonds, A.K., et al., "Use of Expandable Metal Stents in the Treatment of Bronchial Obstruction," *Thorax*, 44: 680, May 1989.

Smith, D., et al., "Safe and Effective Catheter Angiography Through Prosthetic Vascular Grafts," *Radiology*, 138, No. 2: 487-488, Feb. 1981.

Solberg, S., et al., "Cold Induced Endothelial Cell Detachment in Human Sephenous Vein Grafts," *Journal of Cardiovascular*, 28, No. 5: 571-575, Sep.-Oct. 1987.

Soviet Inventions Illustrated, week 84, Jan. 16, 1985, No. 48, M21 P51, Derwent Publications Ltd., London, GB.

Stack, R., et al., "A New Highly Flexible Balloon-Expandable Endovascular Stent: Initial Experimental Results and Up To Six Months Follow-up," *Laser One Meeting*, Newport Beach, California, May 11-13, 1989.

Strecker, E., "A New Vascular Balloon-expandable Prosthesis—Experimental Studies and First Clinical Results," *Journal of Interventional Radiology*, 3: 59-62, 1988.

Strecker, E., et al., "Perkutan Implantierbare, Durth Balloon Aufdehnbare Gefa.beta.prothese," *Dtsch Med Wschr*, 113, No. 4, 538-542, 1988.

Strupp, G., et al., "Clinical and Angiographic Short and Medium Term Results After Coronary Stenting," *Z kardiol*, 81: 500, 1992 (German with English language summary).

Teplick, S., et al., "A New Biliary Endoprosthesis," *American Journal of Roentgenology*, 141: 799-801, Oct. 1983.

Timoshenko, S.P., *Strength of Materials*, Part I, Elementary Theory and Problems, 1930.

Timoshenko, S.P., *Theory of Elastic Stability*, 1961.

Topol, E., *Textbook of Interventional Cardiology*, Chapter 30, by S. Ellis, 623-632, 1990.

Toshiyuki, I., et al., "Relocatable Gianturco Expandable Metallic Stents," *Radiology*, 178: 575, Feb. 1991.

Trent, M., et al., "A Balloon-Expandable Intravascular Stent for Obliterating Experimental Aortic Dissection," *Journal of Vascular Surgery*, 11: 707-717, May 1990.

Uchida, B., et al., "Modifications of Gianturco Expandable Wire Stents," *American Journal of Roentgenology*, 150: 1185-1187, 1988.

Van Der Giessen, W., et al., "Coronary Stenting With a New, Radiopaque, Ballon-Expandable Endoprosthesis in Pigs," *Circulation*, 83: 1788-1798, 1991.

Yoshimura, H., et al., "Afterloading Intracavitary Irradiation and Expanding stent for Malignant Biliary Obstruction," Radiation Medicine, 7: 36-41, 1989.

Yoshioka, T., et al., "Development and Clinical Application of Biliary Endoprosthesis Using Expandable Metallic Stents," *Japan Radiological Society*, 48: 1183-1185, 1988.

Yoshioka, T., et al., "Expandable Metallic Biliary Endoprostheses: Preliminary Clinical Evaluation," *Radiology*, 117: 253-257, 1990.

Yoshioka, T., et al., "Self-Expanding Endovascular Graft: An Experimental Study in Dogs," *AJR*, 151: 673-676, 1988.

Request for *Inter Partes* Reexamination of U.S. Patent No. 6,432,133 dated Mar. 30, 2007 and Exhibits 1-24.

Order Granting/Denying Request for *Inter Partes* Reexamination dated Apr. 24, 2007.

Dorland's Illustration Medical Dictionary, Twenty-sixth Edition, W.B. Saunders Company, pp. 675 and 759, Undated.

Bard, C.R., "PE Plus Peripheral Balloon Dilatation Catheter," *C.R. Bard, Inc.*, 1985.

*Advanced Cardiovascular Systems, Inc. and Guidant Sales Corporation v. Medtronic Vascular, Inc. and Medtronic USA, Inc.*, CA No. 98-80 (SLR) ACS'S Response to Medtronic's Supplemental Submission (Jan. 4, 2007).

*Advanced Cardiovascular Systems, Inc. and Guidant Sales Corporation v. Scimed Life Systems, Inc. and Boston Scientific Corporation*, CA No. IP 98-1108-C-H/G, Deposition of Lilip Lau (vol. I), Jun. 10, 1999 (pp. 1-151).

*Advanced Cardiovascular Systems, Inc. and Guidant Sales Corporation v. Scimed Life Systems, Inc. and Boston Scientific Corporation*, CA No. IP 98-1108-0C-H/G, Deposition of Lilip Lau (vol. II), Jun. 11, 1999 (pp. 252-408).

*Advanced Cardiovascular Systems, Inc. v. Scimed Life Systems, Inc.*, CA No. IP 98-1108-C-H/G, Deposition of David J. Duquette (vol. 1), Dec. 10, 1999 (pp. 1-276).

* cited by examiner

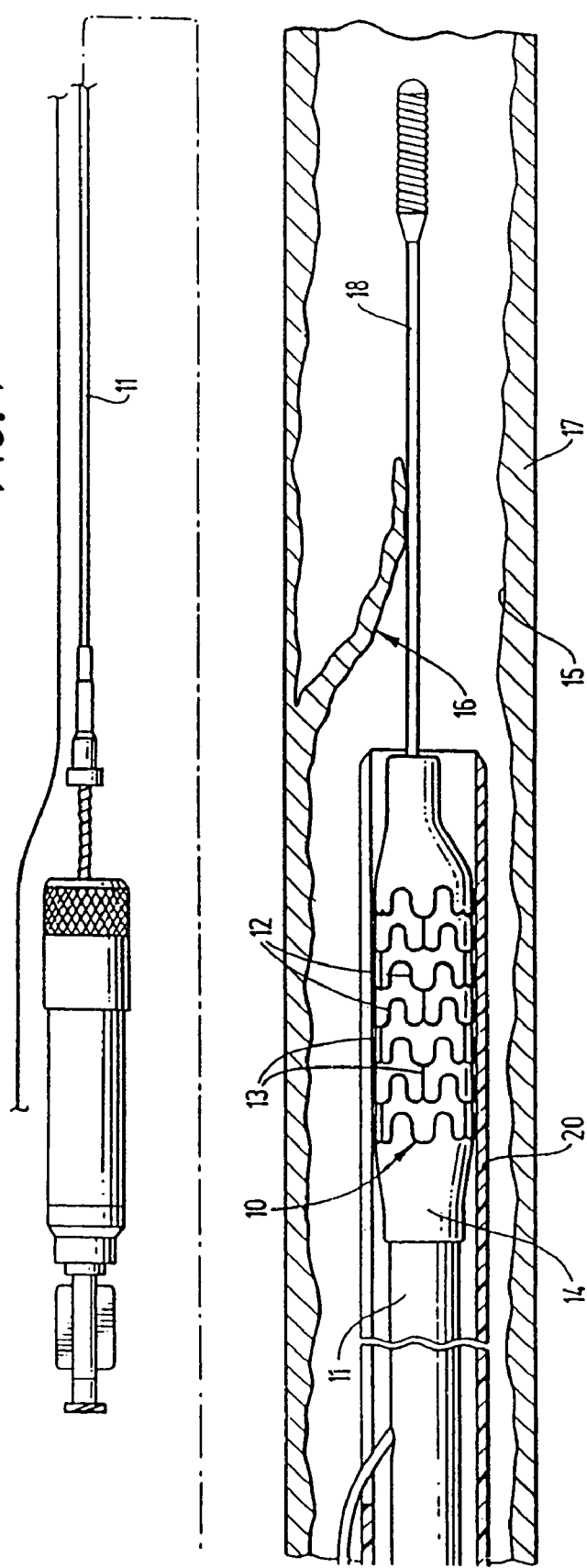
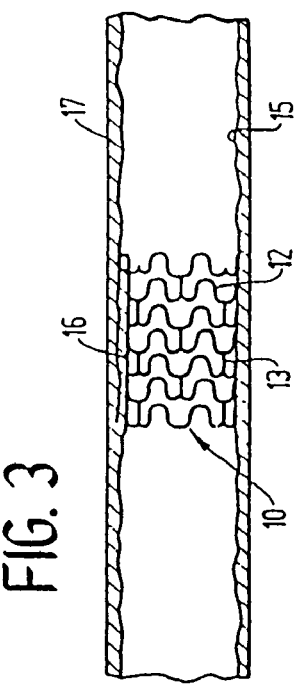
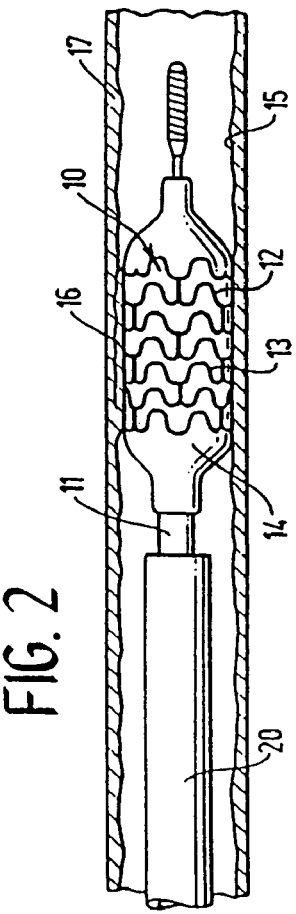

EXPANDABLE STENTS AND METHOD FOR MAKING SAME

RELATED APPLICATIONS

This application is a division of U.S. Ser. No. 10/427,514 filed May 1, 2003 now U.S. Pat. No. 6,908,479 which is a division of U.S. Ser. No. 09/779,078 filed Feb. 8, 2001 now U.S. Pat. No. 6,596,022, which is a division of U.S. Ser. No. 09/561,098 filed Apr. 28, 2000 now U.S. Pat. No. 6,309,412, which is a division of U.S. Ser. No. 09/135,222 filed Aug. 17, 1998 now U.S. Pat. No. 6,056,776, which is a division of U.S. Ser. No. 09/055,582 filed Apr. 6, 1998 now U.S. Pat. No. 6,066,168, which is a division of U.S. Ser. No. 08/783,097 filed Jan. 14, 1997, now U.S. Pat. No. 5,735,893, which is a division of U.S. Ser. No. 08/556,516, filed Nov. 13, 1995, now U.S. Pat. No. 5,603,721, which is a division of U.S. Ser. No. 08/281,790, filed Jul. 28, 1994, now U.S. Pat. No. 5,514,154, which is a continuation in part of U.S. Ser. No. 08/164,986 filed Dec. 9, 1993, now abandoned, which is a continuation of Ser. No. 07/783,558, filed Oct. 28, 1991, now abandoned.

BACKGROUND OF THE INVENTION

This invention relates to expandable endoprosthesis devices, generally called stents, which are adapted to be implanted into a patient's body lumen, such as blood vessel, to maintain the patency thereof. These devices are very useful in the treatment of atherosclerotic stenosis in blood vessels.

Stents are generally tubular-shaped devices which function to hold open a segment of a blood vessel or other anatomical lumen. They are particularly suitable for use to support and hold back a dissected arterial lining which can occlude the fluid passageway therethrough.

Further details of prior art stents can be found in U.S. Pat. No. 3,868,956 (Alfidi et al.); U.S. Pat. No. 4,512,338 (Balko et al.); U.S. Pat. No. 4,553,545 (Maass et al.); U.S. Pat. No. 4,733,665 (Palmaz); U.S. Pat. No. 4,762,128 (Rosenbluth); U.S. Pat. No. 4,800,882 (Gianturco); U.S. Pat. No. 4,856,516 (Hillstead); and U.S. Pat. No. 4,886,062 (Wiktor), which are hereby incorporated herein in their entirety by reference thereto.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter. One of the difficulties encountered using prior stents involved maintaining the radial rigidity needed to hold open a body lumen while at the same time maintaining the longitudinal flexibility of the stent to facilitate its delivery.

What has been needed and heretofore unavailable is a stent which has a high degree of flexibility so that it can be advanced through tortuous passageways and can be readily expanded and yet have the mechanical strength to hold open the body lumen into which it expanded. The present invention satisfies this need.

SUMMARY OF THE INVENTION

The present invention is directed to an expandable stent which is relatively flexible along its longitudinal axis to facilitate delivery through tortuous body lumens, but which is stiff and stable enough radially in an expanded condition to maintain the patency of a body lumen such as an artery when implanted therein.

The stent of the invention generally includes a plurality of radially expandable cylindrical elements which are relatively independent in their ability to expand and to flex relative to one another. The individual radially expandable cylindrical elements of the stent are dimensioned so as to be longitudinally shorter than their own diameters. Interconnecting elements or struts extending between adjacent cylindrical elements provide increased stability and a preferable position to prevent warping of the stent upon the expansion thereof. The resulting stent structure is a series of radially expandable cylindrical elements which are spaced longitudinally close enough so that small dissections in the wall of a body lumen may be pressed back into position against the lumenal wall, but not so close as to compromise the longitudinal flexibilities of the stent. The individual cylindrical elements may rotate slightly relative to adjacent cylindrical elements without significant deformation, cumulatively giving a stent which is flexible along its length and about its longitudinal axis but is still very stiff in the radial direction in order to resist collapse.

The stent embodying features of the invention can be readily delivered to the desired lumenal location by mounting it on an expandable member of a delivery catheter, for example a balloon, and passing the catheter-stent assembly through the body lumen to the implantation site. A variety of means for securing the stent to the expandable member on the catheter for delivery to the desired location are available. It is presently preferred to compress the stent onto the balloon. Other means to secure the stent to the balloon include providing ridges or collars on the inflatable member to restrain lateral movement, or using bioresorbable temporary adhesives.

The presently preferred structure for the expandable cylindrical elements which form the stents of the present invention generally circumferential undulating pattern, e.g. serpentine. The transverse cross-section of the undulating component of the cylindrical element is relatively small and preferably has an aspect ratio of about two to one to about 0.5 to one. A one to one aspect ratio has been found particularly suitable. The open reticulated structure of the stent allows for the profusion of blood over a large portion of the arterial wall which can improve the healing and repair of a damaged arterial lining.

The radial expansion of the expandable cylinder deforms the undulating pattern thereof similar to changes in a waveform which result from decreasing the waveform's amplitude and the frequency. Preferably, the undulating patterns of the individual cylindrical structures are in phase with each other in order to prevent the contraction of the stent along its length when it is expanded. The cylindrical structures of the stent are plastically deformed when expanded (except with NiTi alloys) so that the stent will remain in the expanded condition and therefore they must be sufficiently rigid when expanded to prevent the collapse thereof in use. During expansion of the stent, portions of the undulating pattern will tip outwardly resulting in projecting members on the outer surface of the expanded stent. These projecting members tip radially outwardly from the outer surface of the stent and embed in the vessel wall and help secure the expanded stent so that it does not move once it is implanted.

With superelastic NiTi alloys, the expansion occurs when the stress of compression is removed so as to allow the phase transformation from austenite back to martensite and as a result the expansion of the stent.

The elongated elements which interconnect adjacent cylindrical elements should have a transverse cross-section similar to the transverse dimensions of the undulating components of the expandable cylindrical elements. The interconnecting elements may be formed in a unitary structure with the expandable cylindrical elements from the same intermediate product, such as a tubular element, or they may be formed independently and connected by suitable means, such as by welding or by mechanically securing the ends of the interconnecting elements to the ends of the expandable cylindrical elements. Preferably, all of the interconnecting elements of a stent are joined at either the peaks or the valleys of the undulating structure of the cylindrical elements which for the stent. In this manner there is no shortening of the stent upon expansion.

The number and location of elements interconnecting adjacent cylindrical elements can be varied in order to develop the desired longitudinal flexibility in the stent structure both in the unexpanded as well as the expanded condition. These properties are important to minimize alteration of the natural physiology of the body lumen into which the stent is implanted and to maintain the compliance of the body lumen which is internally supported by the stent. Generally, the greater the longitudinal flexibility of the stent, the easier and the more safely it can be delivered to the implantation site.

In a presently preferred embodiment of the invention the stent is conveniently and easily formed by coating stainless steel tubing with a material resistant to chemical etching, removing portions of the coating to expose portions of underlying tubing which are to be removed to develop the desired stent structure. The exposed portions of the tubing are removed by chemically etching from the tubing exterior leaving the coated portion of the tubing material in the desired pattern of the stent structure. The etching process develops smooth openings in the tubing wall without burrs or other artifacts which are characteristic of mechanical or laser machining processes in the small sized products contemplated. Moreover, a computer controlled laser patterning process to remove the chemical resistive coating makes photolithography technology adaptable to the manufacture of these small products. The forming of a mask in the extremely small sizes needed to make the small stents of the invention would be a most difficult task. A plurality of stents can be formed from one length of tubing by repeating the stent pattern and providing small webs or tabs to interconnect the stents. After the etching process, the stents can be separated by severing the small webs or tabs which connect them.

Other features and advantages of the present invention will become more apparent from the following detailed description of the invention. When taken in conjunction with the accompanying exemplary drawings.

BRIEF DESCRIPTION OF THE DRAWINGS

FIG. 1 is an elevational view, partially in section, of a stent embodying features of the invention which is mounted on a delivery catheter and disposed within a damaged artery.

FIG. 2 is an elevational view, partially in section, similar to that shown in FIG. 1 wherein the stent is expanded within a damaged artery, pressing the damaged lining against the arterial wall.

FIG. 3 is an elevational view, partially in section showing the expanded stent within the artery after withdrawal of the delivery catheter.

DETAILED DESCRIPTION OF THE PREFERRED EMBODIMENTS

Figure 4:
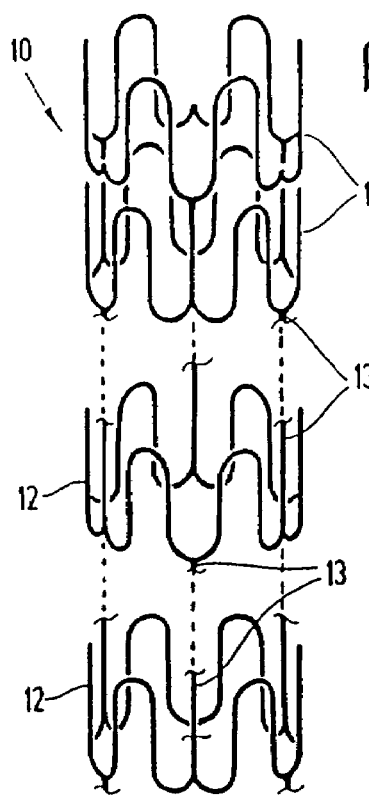
FIG. 4 is a perspective view of a stent embodying features of the invention in an unexpanded state, with one end of the stent being shown in an exploded view illustrate the details thereof.

FIG. 1 illustrates a stent 10 incorporating features of the invention which is mounted onto a delivery catheter 11. The stent generally comprises a plurality of radially expandable cylindrical elements 12 disposed generally coaxially and interconnected by elements 13 disposed between adjacent cylindrical elements. The delivery catheter 11 has an expandable portion or balloon 14 for expanding of the stent 10 within an artery 15. The artery 15, as shown in FIG. 1 has a dissected lining 16 which has occluded a portion of the arterial passageway.

The delivery catheter 11 onto which the stent 10 is mounted, is essentially the same as a conventional balloon dilatation catheter for angioplasty procedures. The balloon 14 may be formed of suitable materials such as polyethylene, polyethylene terephthalate, polyvinyl chloride, nylon and ionomers such as Surlyn® manufactured by the Polymer Products Division of the Du Pont Company. Other polymers may also be used. In order for the stent 10 to remain in place on the balloon 14 during delivery to the site of the damage within the artery 15, the stent 10 is compressed onto the balloon. A retractable protective delivery sleeve 20 as described in co-pending application Ser. No. 07/647,464 filed on Apr. 25, 1990 and entitled STENT DELIVERY SYSTEM may be provided to further ensure that the stent stays in place on the expandable portion of the delivery catheter 11 and prevent abrasion of the body lumen by the open surface of the stent 20 during delivery to the desired arterial location. Other means for securing the stent 10 onto the balloon 14 may also be used, such as providing collars or ridges on the ends of the working portion, i.e. the cylindrical portion, of the balloon.

Each radially expandable cylindrical element 12 of the stent 10 may be independently expanded. Therefore, the balloon 14 may be provided with an inflated shape other than cylindrical, e.g. tapered, to facilitate implantation of the stent 10 in a variety of body lumen shapes.

In a preferred embodiment, the delivery of the stent 10 is accomplished in the following manner. The stent 10 is first mounted onto the inflatable balloon 14 on the distal extremity of the delivery catheter 11. The balloon 14 is slightly inflated to secure the stent 10 onto the exterior of the balloon. The catheter-stent assembly is introduced within the patient's vasculature in a conventional Seldinger technique through a guiding catheter (not shown). A guidewire 18 is disposed across the damaged arterial section with the detached or dissected lining 16 and then the catheter-stent assembly is advanced over a guidewire 18 within the artery 15 until the stent 10 is directly under the detached lining 16. The balloon 14 of the catheter is expanded, expanding the stent 10 against the artery 15, which is illustrated in FIG. 2. While not shown in the drawing, the artery 15 is preferably expanded slightly by the expansion of the stent 10 to seat or otherwise fix the stent 10 to prevent movement. In some circumstances during the treatment of stenotic portions of an artery, the artery may have to be expanded considerably in order to facilitate passage of blood or other fluid therethrough.

The stent 10 serves to hold open the artery 15 after the catheter 11 is withdrawn, as illustrated by FIG. 3. Due to the formation of the stent 10 from elongated tubular member, the undulating component of the cylindrical elements of the stent 10 is relatively flat in transverse cross-section, so that when the stent is expanded, the cylindrical elements are pressed into the wall of the artery 15 and as a result do not interfere with the blood flow through the artery 15. The cylindrical elements 12 of stent 10 which are pressed into the wall of the artery 15 will eventually be covered with endothelial cell growth which further minimizes blood flow interference. The undulating portion of the cylindrical sections 12 provide good tacking characteristics to prevent stent movement within the artery. Furthermore, the closely spaced cylindrical elements 12 at regular intervals provide uniform support for the wall of the artery 15, and consequently are well adapted to tack up and hold in place small flaps or dissections in the wall of the artery 15 as illustrated in FIGS. 2 and 3.

FIG. 4 is an enlarged perspective view of the stent 10 shown in FIG. 1 with one end of the stent shown in an exploded view to illustrate in greater detail the placement of interconnecting elements 13 between adjacent radially expandable cylindrical elements 12. Each pair of the interconnecting elements 13 on one side of a cylindrical element 12 are preferably placed to achieve maximum flexibility for a stent. In the embodiment shown in FIG. 4 the stent 10 has three interconnecting elements 13 between adjacent radially expandable cylindrical elements 12 which are 120 degrees apart. Each pair of interconnecting elements 13 on one side of a cylindrical element 12 are offset radially 60 degrees from the pair on the other side of the cylindrical element. The alternation of the interconnecting elements results in a stent which is longitudinally flexible in essentially all directions. Various configurations for the placement of interconnecting elements are possible, and several examples are illustrated schematically in FIGS. 7-10. However, as previously mentioned, all of the interconnecting elements of an individual stent should be secured to either the peaks or valleys of the undulating structural elements in order to prevent shortening of the stent during the expansion thereof.

Figure 10:
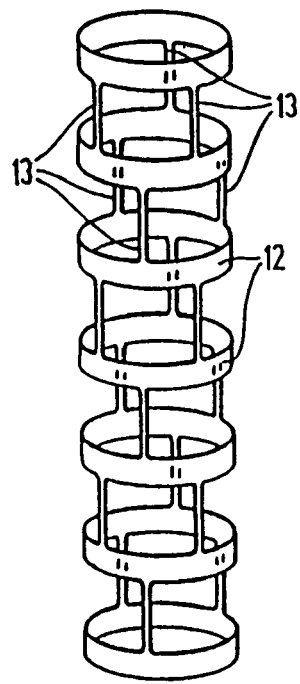

FIG. 10 illustrates a stent of the present invention wherein three interconnecting elements 12 are disposed between radially expandable cylindrical elements 11. The interconnecting elements 12 are distributed radially around the circumference of the stent at a 120-degree spacing. Disposing four or more interconnecting elements 13 between adjacent cylindrical elements 12 will generally give rise to the same considerations discussed above for two and three interconnecting elements.

Figure 11:
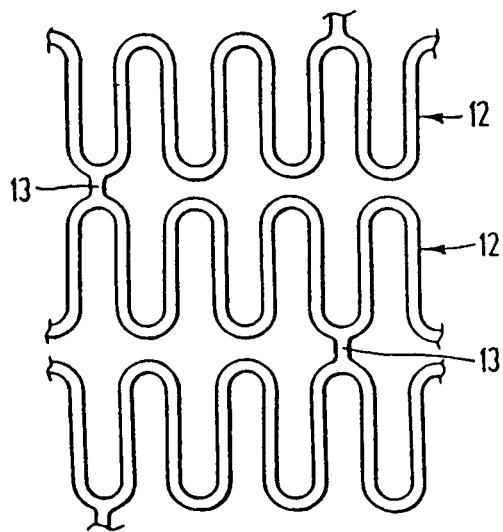
FIG. 11 is a plan view of a flattened section of a stent illustrating an alternate undulating pattern in the expandable cylindrical elements of the stent which are out of phase.
Figure 12:
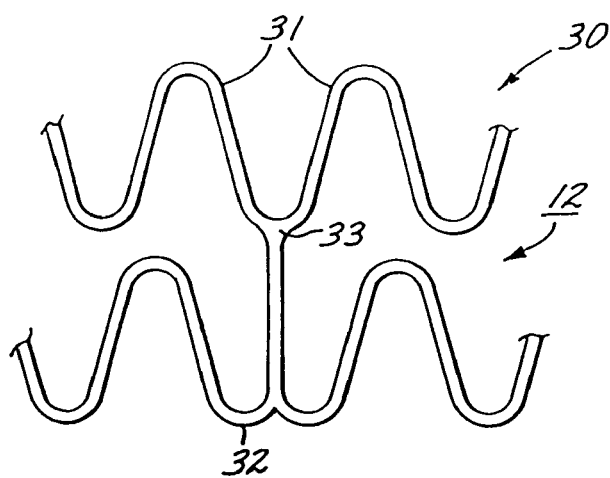
FIG. 12 is an enlarged partial view of the stent of FIG. 5 with the various members slightly expanded.

The properties of the stent 10 may also be varied by alteration of the undulating pattern of the cylindrical elements 13. FIG. 11 illustrates an alternative stent structure in which the cylindrical elements are in serpentine patterns but out of phase with adjacent cylindrical elements. The particular pattern and how many undulations per unit of length around the circumference of the cylindrical element 13, or the amplitude of the undulations, are chosen to fill particular mechanical requirements for the stent such as radial stiffness.

Figure 5:
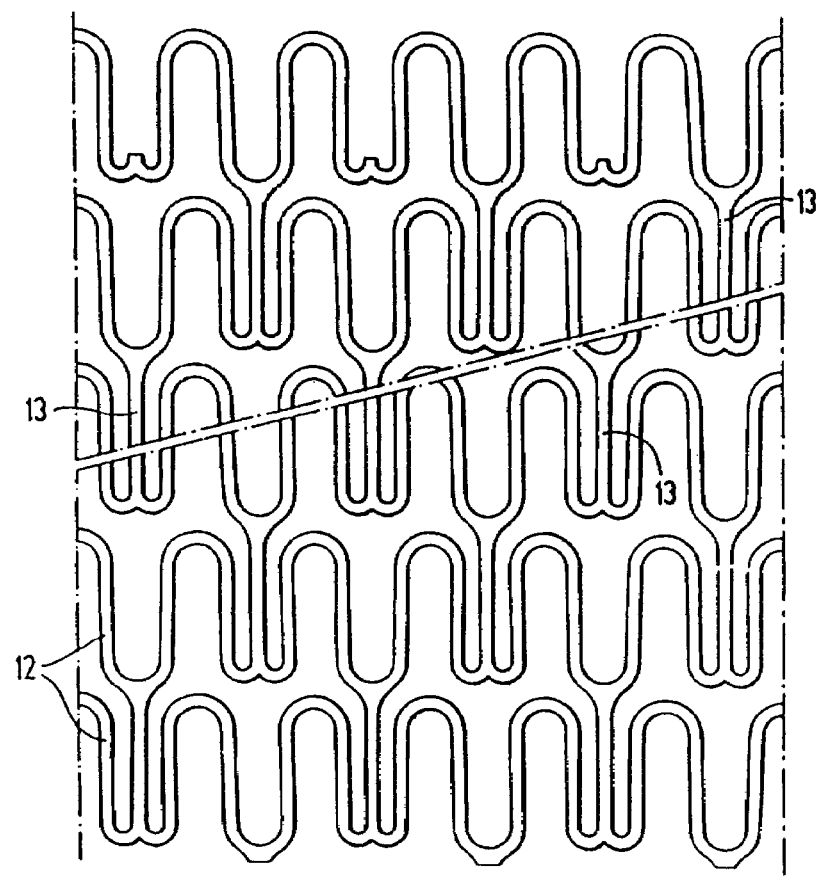
FIG. 5 is a plan view of a flattened section of a stent of the invention which illustrates the undulating pattern of the stent shown in FIG. 4.
Figure 7:
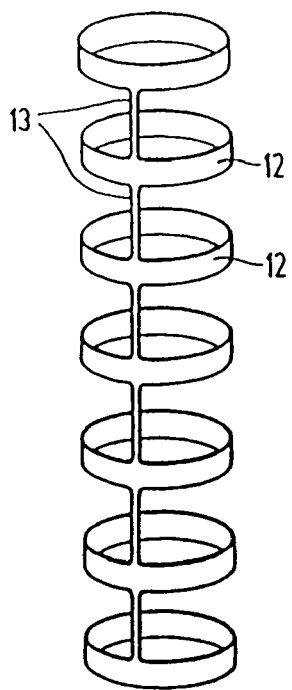
FIGS. 7 through 10 are perspective views schematically illustrating various configurations of interconnective element placement between the radially expandable cylindrical elements of the stent.
Figure 8:
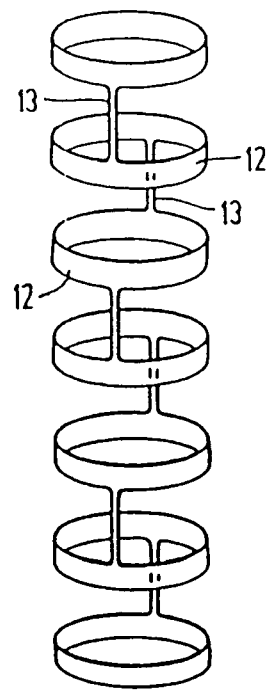
Figure 9:
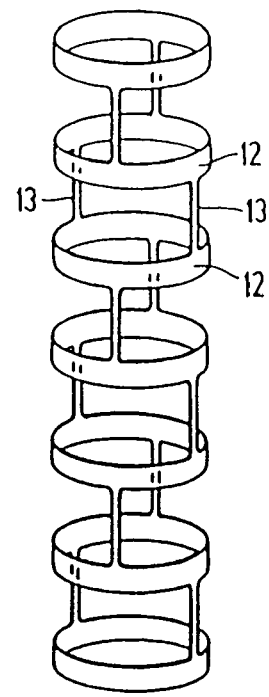

The number of undulations may also be varied to accommodate placement of interconnecting elements 13, e.g. at the peaks of the undulations or along the sides of the undulations as shown in FIGS. 5 and 11.

In keeping with the invention, and with reference to FIGS. 4 and 12-14, cylindrical elements 12 are in the form of a serpentine pattern 30. As previously mentioned, each cylindrical element 12 is connected by interconnecting elements 13. Serpentine pattern 30 is made up of a plurality of U-shaped members 31, W-shaped members 32, and Y-shaped members 33, each having a different radius so that expansion forces are more evenly distributed over the various members.

Figure 13:
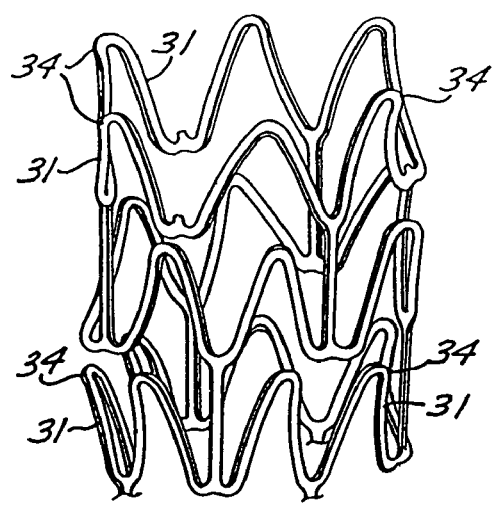
FIG. 13 is a perspective view of the stent of FIG. 4 after it is fully expanded depicting some members projecting radially outwardly.
Figure 14:
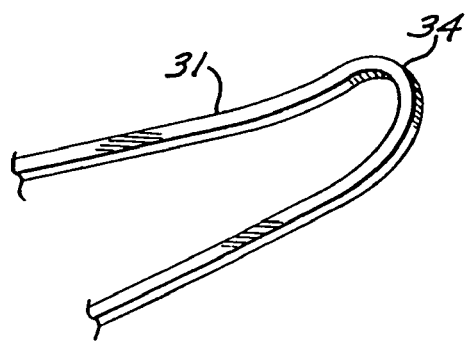
FIG. 14 is an enlarged, partial perspective view of one U-shaped member with its tip projecting outwardly after expansion.

As depicted in FIGS. 13 and 14, after cylindrical elements 12 have been radially expanded, outwardly projecting edges 34 are formed. That is, during radial expansion U-shaped members 31 will tip outwardly thereby forming outwardly projecting edges. These outwardly projecting edges provide for a roughened outer wall surface of stent 10 and assist in implanting the stent in the vascular wall by embedding into the vascular wall. In other words, outwardly projecting edges embed into the vascular wall, for example artery 15, as depicted in FIG. 3. Depending upon the dimensions of stent 10 and the thickness of the various members making up the serpentine pattern 30, any of the U-shaped members 31, W-shaped members 32, and Y-shaped members 33 can tip radially outwardly to form a projecting edge 34. It is most likely and preferred that U-shaped members 31 tip outwardly since they do not join with any connecting member 13 to prevent them from expanding outwardly.

The stent 10 of the present invention can be made in many ways. However, the preferred method of making the stent is to coat a thin-walled tubular member, such as stainless steel tubing, with a material which is resistive to chemical etchants, remove portions of the coating to expose underlying tubing which is to be removed but to leave coated portions of the tubing in the desired pattern for the stent so that subsequent etching will remove the exposed portions of the metallic tubing, but will leave relatively untouched the portions of the metallic tubing which are to form the stent. The coated portion of the metallic tube is in the desired shape for the stent. An etching process avoids the necessity of removing burrs or slag inherent in conventional or laser machining process. It is preferred to remove the etchant-resistive material by means of a machine-controlled laser as illustrated schematically in FIG. 6.

A coating is applied to a length of tubing which, when cured, is resistive to chemical etchants. "Blue Photoresist" made by the Shipley Company in San Jose, Calif., is an example of suitable commercially available photolithographic coatings. The coating is preferably applied by electrophoretic deposition.

To ensure that the surface finish is reasonably uniform, one of the electrodes used for the electrochemical polishing is a doughnut-shaped electrode which is placed about the central portion of the tubular member.

The tubing may be made of suitable biocompatible material such as stainless steel, titanium, tantalum, superelastic NiTi alloys and even high strength thermoplastic polymers. The stent diameter is very small, so the tubing from which it is made must necessarily also have a small diameter. Typically the stent has an outer diameter on the order of about 0.06 inch in the unexpanded condition, the same outer diameter of the tubing from which it is made, and can be expanded to an outer diameter of 0.1 inch or more. The wall thickness of the tubing is about 0.003 inch. In the instance when the stent was plastic, it would have to be heated within the arterial site where the stent is expanded to facilitate the expansion of the stent. Once expanded, it would then be cooled to retain its expanded state. The stent may be conveniently heated by heating the fluid within the balloon or the balloon directly by a suitable system such as disclosed in a co-pending application Ser. No. 07/521,337, filed Jan. 26, 1990 entitled DILATATION CATHETER ASSEMBLY WITH HEATED BALLOON which is incorporated herein in its entirety by reference. The stent may also be made of materials such as superelastic NiTi alloys such as described in co-pending application Ser. No. 07/629,381, filed Dec. 18, 1990, entitled SUPERELASTIC GUIDING MEMBER which is incorporated herein in its entirety by reference. In this case the stent would be formed full size but deformed (e.g. compressed) into a smaller diameter onto the balloon of the delivery catheter to facilitate transfer to a desired intraluminal site. The stress induced by the deformation transforms the stent from a martensite phase to an austenite phase and upon release of the force, when the stent reaches the desired intraluminal location, allows the stent to expand due to the transformation back to the martensite phase.

Figure 6:
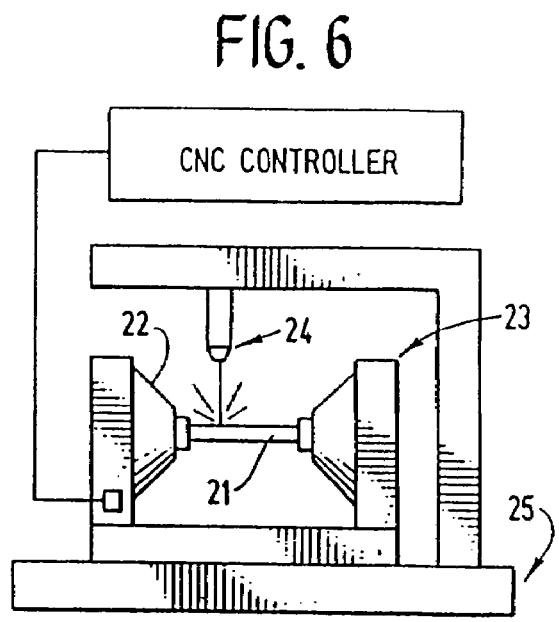
FIG. 6 is a schematic representation of equipment for selectively removing coating applied to tubing in the manufacturing of the stents of the present invention.

Referring to FIG. 6, the coated tubing 21 is put in a rotatable collet fixture 22 of a machine controlled apparatus 23 for positioning the tubing 21 relative to a laser 24. According to machine-encoded instructions, the tubing 21 is rotated and moved longitudinally relative to the laser 24 which is also machine controlled. The laser selectively removes the etchant-resistive coating on the tubing by ablation and a pattern is formed such that the surface of the tube that is to be removed by a subsequent chemical etching process is exposed. The surface of the tube is therefore left coated in the discrete pattern of the finished stent.

A presently preferred system for removing the coating on the tubing includes the use an 80-watt $CO_2$ laser, such as a Coherent Model 44, in pulse mode (0.3 mS pulse length); 48 mA key current and 48 W key power with 0.75 W average power, at 100 Hz; Anorad FR=20; 12.5 Torr; with no assist gas. Low pressure air is directed through the fine focus head to ensure that no vapor contacts the lens. The assist gas jet assembly on the laser unit may be removed to allow a closer proximity of the fine focus head and the collet fixture. Optimum focus is set at the surface of the tubing. Cured photoresist coating readily absorbs the energy of the $CO_2$ wavelength, so that it can be readily removed by the laser. A coated 4-inch length of 0.06 inch stainless steel tubing is preferred and four stents can be patterned on the length of tubing. Three tabs or webs between stents provide good handling characteristics for the tubing after the etching process.

The process of patterning the resistive coating on the stent is automated except for loading and unloading the length of tubing. Referring again to FIG. 6 it may be done, for example, using a CNC-opposing collet fixture 22 for axial rotation of the length of tubing, in conjunction with a CNC X/Y table 25 to move the length of tubing axially relative to a machine-controlled laser as described. The entire space between collets can be patterned using the $CO_2$ laser set-up of the foregoing example. The program for control of the apparatus is dependent on the particular configuration used and the pattern to be ablated in the coating, but is otherwise conventional.

This process makes possible the application of present photolithography technology in manufacturing the stents. While there is presently no practical way to mask and expose a tubular photo-resist coated part of the small size required for making intravascular stents, the foregoing steps eliminate the need for conventional masking techniques.

After the coating is thus selectively ablated, the tubing is removed from the collet fixture 22. Next, wax such at ThermoCote N-4 is heated to preferably just above its melting point, and inserted into the tubing under vacuum or pressure. After the wax has solidified upon cooling, it is reheated below its melting point to allow softening, and a smaller diameter stainless steel shaft is inserted into the softened wax to provide support. The tubing is then etched chemically in a conventional manner. After cutting the tabs connecting the stents any surface roughness or debris from the tabs is removed. The stents are preferably electrochemically polished in an acidic aqueous solution such as a solution of ELECTRO-GLO #300, sold by the ELECTRO-GLO CO., Inc. in Chicago, Ill., which is a mixture of sulfuric acid, carboxylic acids, phosphates, corrosion inhibitors and a biodegradable surface active agent. The bath temperature is maintained at about 110-135 degrees F. and the current density is about 0.4 to about 1.5 amps per in.$^2$ Cathode to anode area should be at least about two to one. The stents may be further treated if desired, for example by applying a biocompatible coating.

While the invention has been illustrated and described herein in terms of its use as an intravascular stent, it will be apparent to those skilled in the art that the stent can be used in other instances such as to expand prostatic urethras in cases of prostate hyperplasia. Other modifications and improvements may be made without departing from the scope of the invention.

Other modifications and improvements can be made to the invention without departing from the scope thereof.

What is claimed is:

1. A method of chemically etching a metallic member to form an intravascular stent, comprising:

applying a photoresistive coating to a metallic surface of the metallic member;

selectively removing portions of the photoresistive coating from the metallic surface thereby providing exposed portions of the metallic surface and protected portions of the metallic surface;

exposing the metallic surface to a chemical etchant solution thereby removing a full thickness of the metallic member to form a pattern generally corresponding to the exposed portions of the metallic surface;

removing the photoresistive coating; and electrochemically polishing the metallic member in a solution having at least an acid and a corrosion inhibitor.

2. The method of claim 1, wherein the metallic surface is curved and selective removal of portions of the resistive coating from the curved metallic surface provides the stent pattern.

3. The method of claim 2, wherein the curved metallic surface is in the form of a tubular member and the photoresistive coating is applied to an outer surface of the tubular member.

4. The method of claim 3, wherein prior to removing selected portions of the photoresistive coating, inserting a substance into the tubular member to protect an inner surface of the tubular member from the chemical etchant solution.

5. The method of claim 4, wherein softened wax is inserted into the tubular member.

* * * * *